United States Patent
Chon

(10) Patent No.: US 8,403,951 B2
(45) Date of Patent: Mar. 26, 2013

(54) PHACOEMULSIFICATION TIP

(75) Inventor: James Y. Chon, Irvine, CA (US)

(73) Assignee: Novartis AG, Basel (CH)

( * ) Notice: Subject to any disclaimer, the term of this patent is extended or adjusted under 35 U.S.C. 154(b) by 2044 days.

(21) Appl. No.: 11/074,739

(22) Filed: Mar. 8, 2005

(65) Prior Publication Data

US 2006/0217672 A1     Sep. 28, 2006

(51) Int. Cl.
*A61B 17/32* (2006.01)
*A61M 37/00* (2006.01)

(52) U.S. Cl. .......................... 606/171; 604/22

(58) Field of Classification Search .............. 604/22; 606/166, 169–171
See application file for complete search history.

(56) References Cited

U.S. PATENT DOCUMENTS

| | | | |
|---|---|---|---|
| 3,589,363 A | 6/1971 | Banko et al. | |
| 4,223,676 A | 9/1980 | Wuchinich et al. | |
| 4,246,902 A | 1/1981 | Martinez | |
| 4,445,509 A * | 5/1984 | Auth | 606/159 |
| 4,493,694 A | 1/1985 | Wuchinich | |
| 4,515,583 A | 5/1985 | Sorich | |
| 4,589,415 A | 5/1986 | Haaga | |
| 4,609,368 A | 9/1986 | Dotson, Jr. | |
| 4,816,018 A | 3/1989 | Parisi | |
| 4,869,715 A | 9/1989 | Sherburne | |
| 4,922,902 A | 5/1990 | Wuchinich et al. | |
| 4,989,583 A | 2/1991 | Hood | |
| 5,154,694 A | 10/1992 | Kelman | |
| 5,282,847 A * | 2/1994 | Trescony et al. | 623/1.29 |
| 5,359,996 A | 11/1994 | Hood | |
| 5,653,724 A | 8/1997 | Imonti | |
| 5,733,297 A * | 3/1998 | Wang | 606/167 |
| 6,039,715 A | 3/2000 | Mackool | |
| 6,077,285 A | 6/2000 | Boukhny | |
| 6,126,629 A | 10/2000 | Perkins | |
| 6,196,989 B1 * | 3/2001 | Padget et al. | 604/27 |
| 6,352,519 B1 | 3/2002 | Anis et al. | |
| 6,398,759 B1 * | 6/2002 | Sussman et al. | 604/114 |
| 6,602,193 B2 | 8/2003 | Chon | |
| 6,648,847 B2 | 11/2003 | Sussman | |
| 2004/0193121 A1 | 9/2004 | Kadziauskas et al. | |
| 2004/0249306 A1 * | 12/2004 | Islam | 600/567 |
| 2006/0052758 A1 * | 3/2006 | Dewey | 604/272 |

* cited by examiner

*Primary Examiner* — Nicholas Lucchesi
*Assistant Examiner* — Nathan R Price
(74) *Attorney, Agent, or Firm* — Kenneth Bassinger

(57) ABSTRACT

A phacoemulsification tip having a crimped or swaged distal tip. Swaging of the distal end of a phacoemulsification tip produces more efficient cutting during torsional vibration of the tip by increasing the cutting surface area.

3 Claims, 3 Drawing Sheets

PHACOEMULSIFICATION TIP

BACKGROUND OF THE INVENTION

This invention relates generally to the field of phacoemulsification and more particularly to torsional phacoemulsification cutting tips.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an IOL.

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

One phacoemulsification tip that has gained widespread acceptance has a belled or flared distal end. Such a tip is described in U.S. Pat. No. 4,816,018 (Parisi). Such a design allows for larger lens material purchase as well as increased holding force when vacuum is applied to the tip while maintaining a smaller bore in the shaft of the tip. This combination of features increases anterior chamber stability, by reducing sudden outflow from the anterior chamber when the distal end becomes occluded and this occlusion breaks.

Another phacoemulsification tip is an angled or "bent" tip with or without a flared distal end. These tips are described in U.S. Pat. No. 6,039,715 (Mackool), U.S. Pat. No. 5,653,724 (Imonti) and U.S. Pat. No. 5,154,694 (Kelman). These tips have a predominantly straight shaft with the far distal portion of the shaft being bent on an angle. Bent tips are used by a great many surgeons, and are particularly useful when used in conjunction with a oscillatory phacoemulsification handpiece, such as those described in U.S. Pat. No. 6,352,519 (Anis, et al.) and U.S. Pat. No. 6,602,193 (Chon) and commercially available as the NeoSoniX® handpiece from Alcon Laboratories, Inc., Fort Worth, Tex., however; some surgeons are reluctant they feel that due to the proximal location of the bend it is more difficult to judge the position of the proximal cutting edge based on the extrapolation of the sleeved portion of the tip.

The inventors have discovered that swaged phacoemulsification tips are particularly advantageous when used in combination with torsional ultrasound handpiece. Torsional ultrasound handpieces are more fully disclosed in U.S. Pat. No. 6,077,285 (Boukhny). Therefore, a need continues to exist for a swaged phacoemulsification tip.

BRIEF SUMMARY OF THE INVENTION

The present invention improves upon the prior art by providing a phacoemulsification tip having a crimped or swaged distal tip. Swaging of the distal end of a phacoemulsification tip produces more efficient cutting during torsional vibration of the tip by increasing the cutting surface area.

Accordingly, one objective of the present invention is to provide a phacoemulsification cutting tip having increased efficiency, particularly during torsional ultrasound movement.

Another objective of the present invention is to provide a phacoemulsification cutting tip having a crimped or swaged distal tip.

These and other advantages and objectives of the present invention will become apparent from the detailed description and claims that follow.

DETAILED DESCRIPTION OF THE INVENTION

Figure 1:
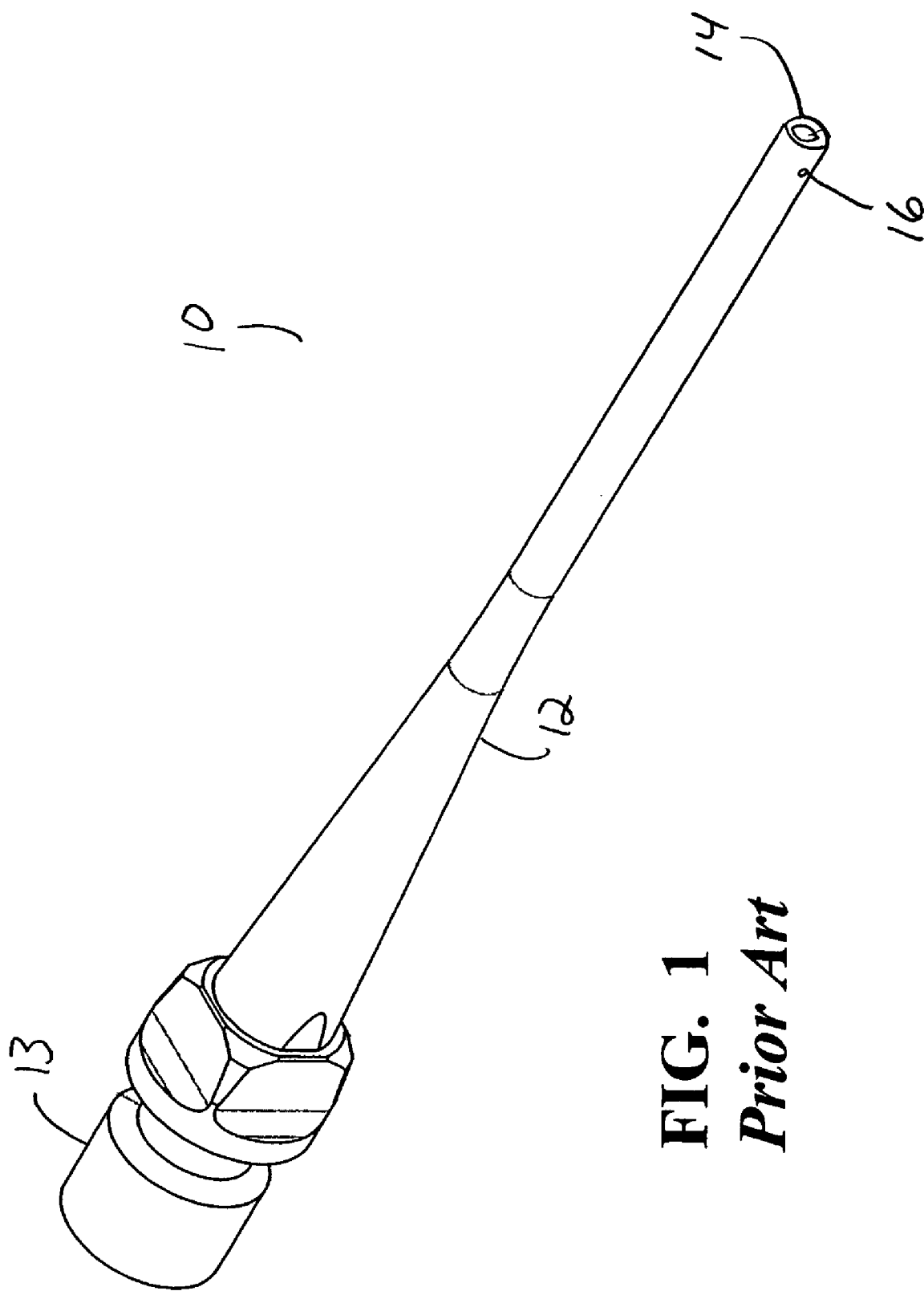
FIG. 1 is an enlarged perspective view of a typical prior art phacoemulsification tip.

As best seen in FIG. 1, prior art phacoemulsification tip 10 contains shaft 12 extending from hub 13. Shaft 12 is straight all the way to distal tip 14. Distal tip 14 may be angled or bent relative to the centerline of shaft 12. Shaft 12 may contain aspiration bypass hole 16.

Figure 2:
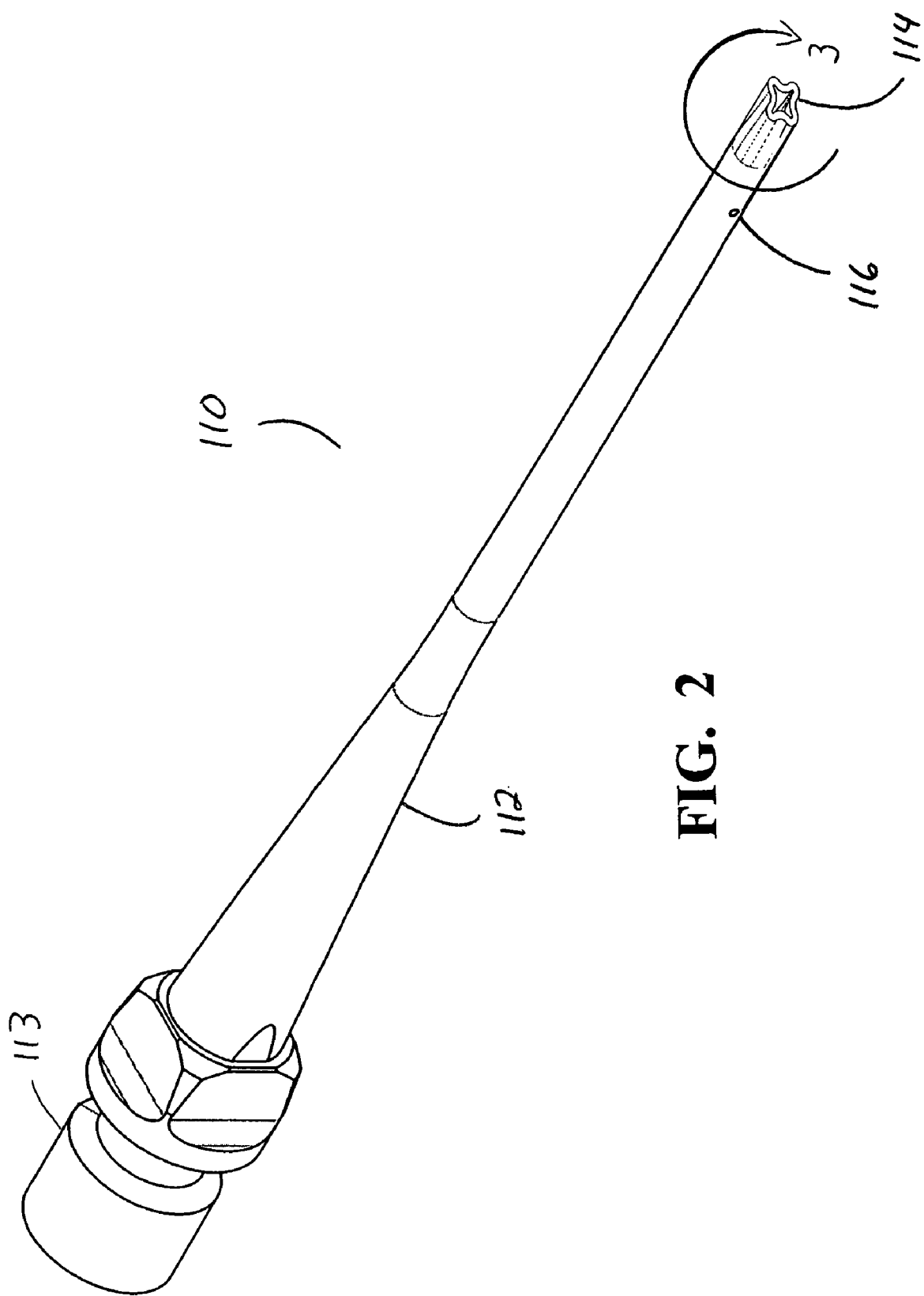
FIG. 2 is an enlarged perspective view of the phacoemulsification tip of the present invention.

As best seen in FIG. 2, phacoemulsification tip 110 contains shaft 112 extending from hub 113. Shaft 112 is straight all the way to distal tip 114. Distal tip 114 may be angled or bent relative to the centerline of shaft 112. Shaft 112 may contain aspiration bypass hole 116.

Figure 3:
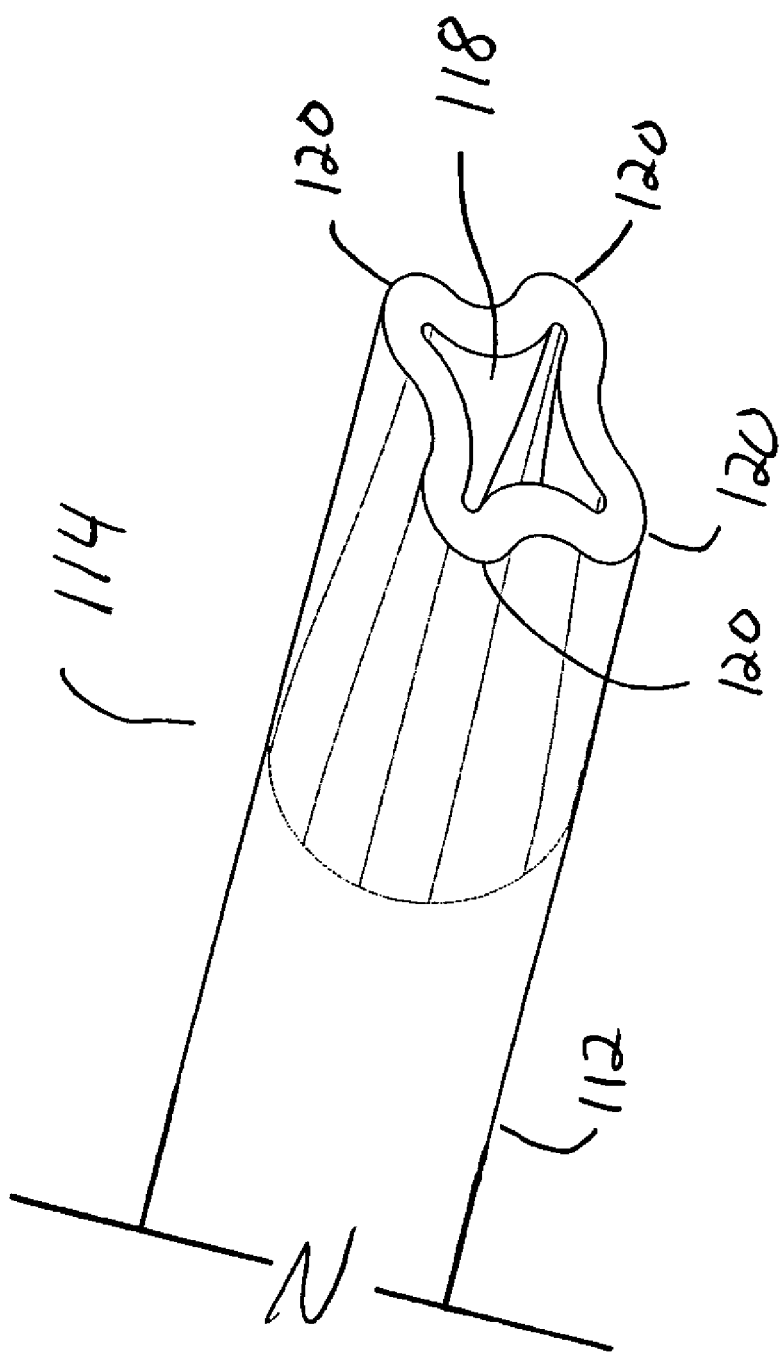
FIG. 3 is an enlarged perspective view of the distal tip of the phacoemulsification tip of the present invention taken at circle 3 in FIG. 2.

As best seen in FIG. 3, distal tip 114 is crimped or swaged so that aspiration port 118 is not round and distal tip 114 contains a plurality of external cutting edges 120. Cutting edges 120 assist in the cutting and emulsification of tissue when tip 110 is ultrasonically vibrated in a torsional or rotational manner. While FIG. 3 shows four fluted cutting edges 120, one skilled in the art will recognize that a various number and style of cutting edges 120 can be formed on distal tip 114 depending upon the metalworking technique used.

Tip 110 is preferably made from stainless steel or titanium, but other materials may also be used. Tip 110 preferably has an overall length of between 0.50 inches and 1.50 inches, with 1.20 inches being most preferred. Tip 110 may be formed using conventional metalworking technology and preferably is electropolished to remove any burrs.

Shaft 112 is generally tubular, with an outside diameter of between 0.005 inches and 0.100 inches and an inside diameter of between 0.001 inches and 0.090 inches. Distal tip 114 may be cut square or cut at any suitable angle between 0° and 90°.

This description is given for purposes of illustration and explanation. It will be apparent to those skilled in the relevant art that changes and modifications may be made to the invention described above without departing from its scope or spirit.

I claim:

1. A phacoemulsification tip, comprising: a tubular shaft having a crimped distal end, the distal end having a plurality of fluted cutting edges, the fluted cutting edges located at a terminal end of the tubular shaft and extending back from the terminal end along the tubular shaft, an exterior surface of the fluted cutting edges exposed along a length of the crimped distal end of the tubular shaft.

2. The phacoemulsification tip of claim 1 wherein the shaft contains an aspiration bypass hole.

3. The phacoemulsification tip of claim 1 wherein the shaft is bent relative to a centerline of the shaft.

\* \* \* \* \*